(12) United States Patent
Al-Jindan et al.

(10) Patent No.: US 12,320,688 B2
(45) Date of Patent: Jun. 3, 2025

(54) SYSTEMS AND METHODS FOR ANALYZING MULTIPHASE PRODUCTION FLUIDS

(71) Applicant: Saudi Arabian Oil Company, Dhahran (SA)

(72) Inventors: Jana M. Al-Jindan, Dammam (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 364 days.

(21) Appl. No.: 17/708,658

(22) Filed: Mar. 30, 2022

(65) Prior Publication Data

US 2023/0314198 A1 Oct. 5, 2023

(51) Int. Cl.
*G01F 1/74* (2006.01)
*E21B 49/08* (2006.01)
(Continued)

(52) U.S. Cl.
CPC ............ *G01F 1/74* (2013.01); *E21B 49/0875* (2020.05); *G01F 1/582* (2013.01); *G01F 1/64* (2013.01); *G01F 23/263* (2013.01)

(58) Field of Classification Search
CPC ................. G01F 1/52; G01F 1/64; G01F 1/74
See application file for complete search history.

(56) References Cited

U.S. PATENT DOCUMENTS 5,394,339 A 2/1995 Jones
11,118,452 B1 9/2021 Yateem et al.
(Continued)

FOREIGN PATENT DOCUMENTS

WO 2013084183 A3 6/2013
WO 20130854183 A3 6/2013
(Continued)

OTHER PUBLICATIONS

International Preliminary Report on Patentability dated Sep. 24, 2024, received in corresponding PCT Application Serial No. PCT/US2023/012469, filed Oct. 5, 2023, pp. 1-13.
(Continued)

*Primary Examiner* — Erika J. Villaluna
(74) *Attorney, Agent, or Firm* — DINSMORE & SHOHL LLP

(57) ABSTRACT

Systems and components thereof are provided for analyzing multiphase production fluids. The system comprises a fluidic separation chamber, a fluidic separation chamber valve, fluidic piping configured to supply multiphase production fluid to the fluidic separation chamber through the fluidic separation chamber valve, a plurality of composite sensing modules vertically spaced within the fluidic separation chamber, and a fluidic supply and analysis unit. Each of the sensing modules comprising an inductive sensor comprising opposing inductive sensing elements displaced from one another across a vertically extending measurement portion of the fluidic separation chamber, and a capacitive sensor comprising opposing capacitive sensing elements displaced from one another across the vertically extending measurement portion of the fluidic separation chamber. The capacitive sensor of each of the plurality of composite sensing modules to detect a height $H_O$ of an oil phase column in the multiphase production fluid in the fluidic separation chamber.

20 Claims, 4 Drawing Sheets

(51) Int. Cl.
    *G01F 1/58*    (2006.01)
    *G01F 1/64*    (2006.01)
    *G01F 23/263*    (2022.01)

(56) References Cited

U.S. PATENT DOCUMENTS

2013/0126183 A1    5/2013  Bell
2023/0408309 A1*   12/2023 Huang .................. G01F 15/063

FOREIGN PATENT DOCUMENTS

| WO | 2013141748 A1 | 9/2013 |
| WO | 2015142610 A1 | 9/2015 |
| WO | 2022047384 A1 | 3/2022 |

OTHER PUBLICATIONS

Notification of Transmittal of the International Search Report and the Written Opinion of the International Searching Authority, or the Declaration dated Jul. 24, 2023 pertaining to International application No. PCT/US2023/012469 filed Feb. 7, 2023, pp. 1-22.

* cited by examiner

SYSTEMS AND METHODS FOR ANALYZING MULTIPHASE PRODUCTION FLUIDS

BACKGROUND

The present disclosure relates to the analysis of multiphase production fluids and, more particularly, to the analysis of multiphase flow in the oil and gas industries, where multiphase flow often involves the simultaneous flow of oil, water and gas.

BRIEF SUMMARY

According to the subject matter of the present disclosure, systems and components thereof are provided for analyzing multiphase production fluids. In accordance with one embodiment of the present disclosure, the system comprises a fluidic separation chamber, a fluidic separation chamber valve, fluidic piping configured to supply multiphase production fluid to the fluidic separation chamber through the fluidic separation chamber valve, a plurality of composite sensing modules vertically spaced within the fluidic separation chamber, and a fluidic supply and analysis unit in communication with the fluidic separation chamber valve and the plurality of composite sensing modules. Each of the sensing modules comprising an inductive sensor comprising opposing inductive sensing elements displaced from one another across a vertically extending measurement portion of the fluidic separation chamber, and a capacitive sensor comprising opposing capacitive sensing elements displaced from one another across the vertically extending measurement portion of the fluidic separation chamber. The fluidic supply and analysis unit is configured to communicate with the fluidic separation chamber valve to supply a multiphase production fluid to the fluidic separation chamber. The fluidic supply and analysis unit is further configured to communicate with the inductive sensor of each of the plurality of composite sensing modules to detect a height $H_W$ of a water phase column in the multiphase production fluid in the fluidic separation chamber. The fluidic supply and analysis unit is further configured to communicate with the capacitive sensor of each of the plurality of composite sensing modules to detect a height $H_O$ of an oil phase column in the multiphase production fluid in the fluidic separation chamber. The fluidic supply and analysis unit is further configured to communicate with the capacitive sensor of each of the plurality of composite sensing modules to detect a height $H_G$ of a gas phase column in the multiphase production fluid in the fluidic separation chamber. The fluidic supply and analysis unit is further configured to convert the height $H_W$ of the water phase column, the height $H_O$ of the oil phase column, and the height $H_G$ of the gas phase column to production fluid phase volume fraction data, production fluid phase flow rate data, or both.

In accordance with another embodiment of the present disclosure, the system comprises fluidic piping, a fluidic separation chamber, a fluidic separation chamber valve, a mechanized composite sensing module, and a fluidic supply and analysis unit. The fluidic piping is configured to supply multiphase production fluid to the fluidic separation chamber through the fluidic separation chamber. The mechanized composite sensing module comprises an inductive sensor and a capacitive sensor and is translatable along a vertically extending measurement portion of the fluidic separation chamber. The inductive sensor comprises opposing inductive sensing elements displaced from one another across the vertically extending measurement portion of the fluidic separation chamber. The capacitive sensor comprises opposing capacitive sensing elements displaced from one another across the vertically extending measurement portion of the fluidic separation chamber. The fluidic supply and analysis unit is in communication with the fluidic separation chamber valve and the mechanized composite sensing module. The fluidic supply and analysis unit is configured to communicate with the fluidic separation chamber valve to supply a multiphase production fluid to the fluidic separation chamber. The fluidic supply and analysis unit is further configured to communicate with the inductive sensor of the mechanized composite sensing module to detect a height $H_W$ of a water phase column in the multiphase production fluid in the fluidic separation chamber during translation of the mechanized composite sensing module along the vertically extending measurement portion of the fluidic separation chamber. The fluidic supply and analysis unit is further configured to communicate with the capacitive sensor of the mechanized composite sensing module to detect a height $H_O$ of an oil phase column in the multiphase production fluid in the fluidic separation chamber during translation of the mechanized composite sensing module along the vertically extending measurement portion of the fluidic separation chamber. The fluidic supply and analysis unit is further configured to communicate with the capacitive sensor of the mechanized composite sensing module to detect a height $H_G$ of a gas phase column in the multiphase production fluid in the fluidic separation chamber during translation of the mechanized composite sensing module along the vertically extending measurement portion of the fluidic separation chamber. The fluidic supply and analysis unit is further configured to convert the height $H_W$ of the water phase column, the height $H_O$ of the oil phase column, and the height $H_G$ of the gas phase column to production fluid phase volume fraction data, production fluid phase flow rate data, or both.

In accordance with a further embodiment of the present disclosure, a fluidic separation chamber is provided comprising a vertically extending measurement portion, a vertically extending dampening portion, a lower fluidic junction positioned vertically below, and an inlet port. The lower fluidic junction fluidly coupling the vertically extending measurement portion and the vertically extending dampening portion. The inlet port being fluidly coupled to the vertically extending dampening portion and the vertically extending measurement portion through the lower fluidic junction. The vertically extending dampening portion, the vertically extending measurement portion, and the fluidic junction are configured such that multiphase production fluid provided to the fluidic separation chamber through the inlet port is free to flow into the vertically extending measurement portion and the vertically extending dampening portion through the fluidic junction. The vertically extending dampening portion, the vertically extending measurement portion, and the fluidic junction are further configured such that the multiphase production fluid assumes a dampened oscillating flow across the lower fluidic junction to force columnar dampening in the vertically extending measurement portion of the fluidic separation chamber.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
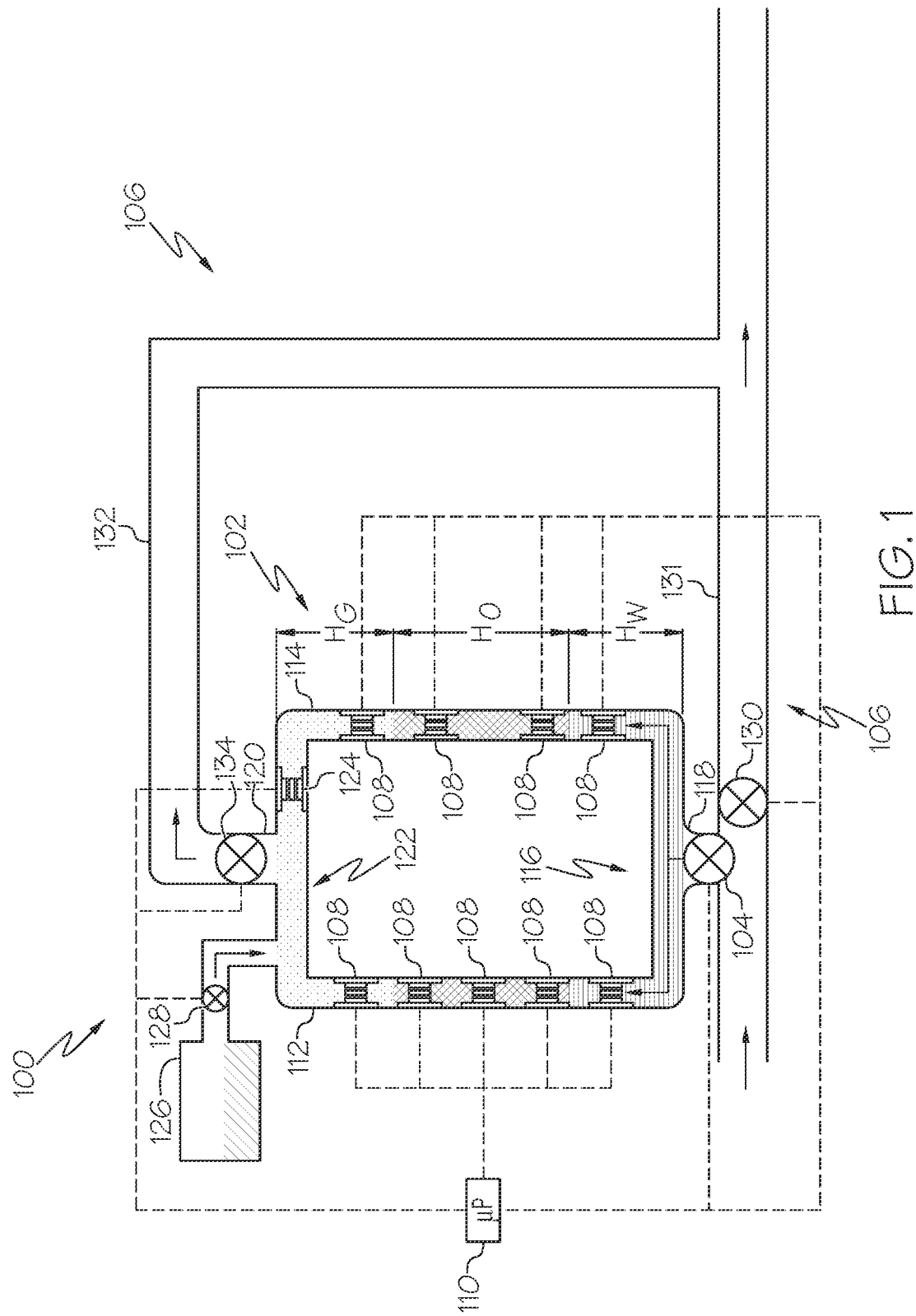
FIG. 1 is a schematic illustration of a system for analyzing a multiphase production fluid according to one or more embodiments of the present disclosure.

Referring initially to FIG. 1, a system 100 for analyzing a multiphase production fluid is shown according to various embodiments. The system 100 comprises a fluidic separation chamber 102, a fluidic separation chamber valve 104, fluidic piping 106, a plurality of composite sensing modules 108, and a fluidic supply and analysis unit 110. The plurality of composite sensing modules 108 are vertically spaced within the fluidic separation chamber 102. The fluidic piping 106 is configured to supply multiphase production fluid to the fluidic separation chamber 102 through the fluidic separation chamber valve 104.

The fluidic separation chamber 102 comprises a vertically extending measurement portion 112. The vertically extending measurement portion 112 may extend entirely along a vertical axis, as is illustrated in FIG. 1, or may merely be inclined with respect to the vertical axis, such that it extends partially along the vertical axis, and partially along a horizontal axis. In embodiments, the vertically extending dampening portion 114 is parallel to the vertically extending measurement portion 112 of the fluidic separation chamber 102.

The fluidic separation chamber 102 may further comprise a vertically extending dampening portion 114, a lower fluidic junction 116, and an inlet port 118. The lower fluidic junction 116 is positioned vertically below the vertically extending measurement portion 112 and the vertically extending dampening portion 114. The lower fluidic junction 116 fluidly coupling the vertically extending measurement portion 112 and the vertically extending dampening portion 114. The lower fluidic junction 116 may comprise a linear length of horizontally oriented fluidic piping. The inlet port 118 is fluidly coupled to the vertically extending dampening portion 114 and the vertically extending measurement portion 112 through the lower fluidic junction 116.

The vertically extending measurement portion 112, the vertically extending dampening portion 114, and the lower fluidic junction 116 may be configured such that multiphase production fluid supplied to the fluidic separation chamber 102 through the inlet port 118 is free to flow into the vertically extending measurement portion 112 and the vertically extending dampening portion 114 through the lower fluidic junction 116. The vertically extending measurement portion 112, the vertically extending dampening portion 114, and the lower fluidic junction 116 may be further configured such that the supplied multiphase production fluid assumes a dampened oscillating flow across the lower fluidic junction 116 to force columnar dampening in the vertically extending measurement portion 112.

The fluidic separation chamber 102 may further comprise an outlet port 120 fluidly coupled to the vertically extending dampening portion 114 and the vertically extending measurement portion 112. The outlet port 120 may be vertically displaced from the inlet port 118 such that the inlet and outlet ports 118,120 are positioned vertically beyond opposite ends of the vertically extending measurement portion 112 and the vertically extending dampening portion 114.

The fluidic separation chamber 102 may further comprise an upper fluidic junction 122 positioned vertically above, and fluidly coupling, the vertically extending measurement portion 112 and the vertically extending dampening portion 114. The outlet port 120 may be fluidly coupled to the vertically extending dampening portion 114 and the vertically extending measurement portion 112 through the upper fluidic junction 122. The upper fluidic junction 122 may comprise a linear length of horizontally oriented fluidic piping.

In embodiments, an additional composite sensing module 124 is disposed along the linear length of horizontally oriented fluidic piping of the upper fluidic junction 122. The additional composite sensing module 124 is communicatively coupled to the fluidic supply and analysis unit 110. By positioning the additional composite sensing module 124 in this location, a gas phase of the multiphase production fluid may be detected in embodiments where an oil phase of the multiphase production fluid occupies an upper portion of the fluidic separation chamber 102.

In embodiments, the plurality of composite sensing modules 108 are disposed both along the vertically extending measurement portion 112 and along the vertically extending dampening portion 114. In embodiments, the vertically extending measurement portion 112 and the vertically extending dampening portion 114 of the fluidic separation chamber 102 define cylindrical cross sections.

Figure 2:
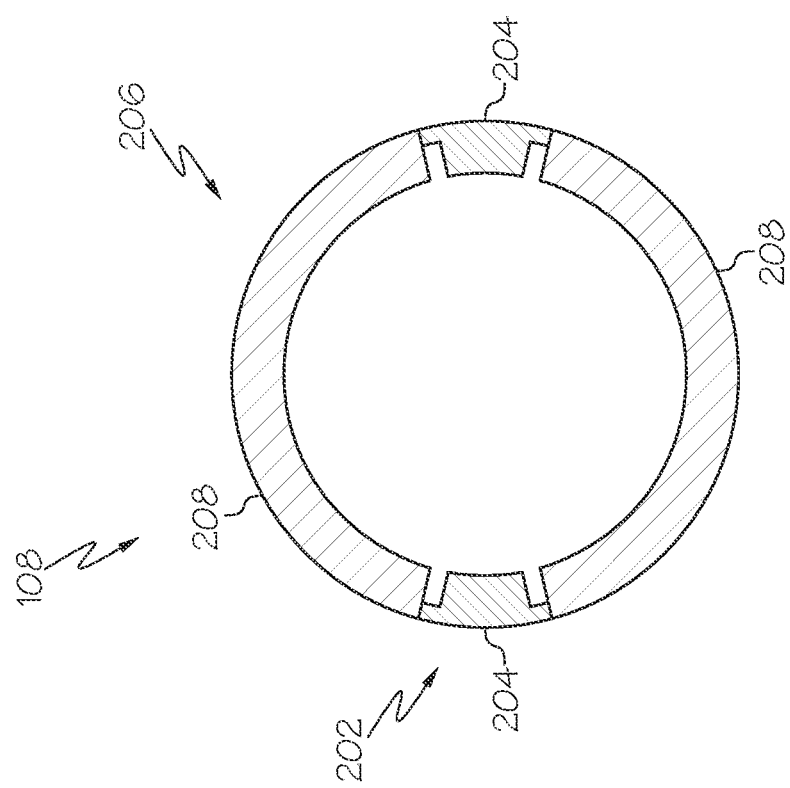
FIG. 2 illustrates aspects of a composite sensing module according to one or more embodiments of the present disclosure.

Referring now to FIG. 2, each of the composite sensing modules 108 comprises an inductive sensor 202 comprising opposing inductive sensing elements 204 displaced from one another across the vertically extending measurement portion 112 of the fluidic separation chamber 102. Each of the composite sensing modules 108 further comprises a capacitive sensor 206 comprising opposing capacitive sensing elements 208 displaced from one another across the vertically extending measurement portion 112 of the fluidic separation chamber 102.

The fluidic supply and analysis unit 110 in communication with the fluidic separation chamber valve 104 and the plurality of composite sensing modules 108. The fluidic supply and analysis unit 110 is configured to communicate with the fluidic separation chamber valve to supply a multiphase production fluid to the fluidic separation chamber 102. The fluidic supply and analysis unit 110 is configured to communicate with the inductive sensor 202 of each of the plurality of composite sensing modules 108 to detect a height $H_W$ of a water phase column in the multiphase production fluid in the fluidic separation chamber. The fluidic supply and analysis unit 110 is further configured to communicate with the capacitive sensor 206 of each of the plurality of composite sensing modules 108 to detect a height $H_O$ of the oil phase column in the multiphase production fluid in the fluidic separation chamber 102. The fluidic supply and analysis unit 110 is further configured to communicate with the capacitive sensor 206 of each of the plurality of composite sensing modules 108 to detect a height $H_G$ of the gas phase column in the multiphase production fluid in the fluidic separation chamber 102. The fluidic supply and analysis unit 110 may be further configured to convert the height $H_W$ of the water phase column, the height $H_O$ of the oil phase column, the height $H_G$ of the gas phase column to production fluid phase volume fraction data.

The fluidic supply and analysis unit 110 is further configured to convert the height $H_W$ of the water phase column, the height $H_O$ of the oil phase column, and the height $H_G$ of the gas phase column to production fluid phase volume fraction data, production fluid phase flow rate data, or both. In embodiments, the fluidic supply and analysis unit 110 is further configured to calculate production fluid phase flow rate data using the phase volume fraction data and a cross-sectional area A of the fluidic piping, the calculation comprising the product of equation 1.

$$A \times (H_W + H_O + H_G) \qquad \text{Equation 1}$$

In embodiments, each of the plurality of composite sensing modules 108 are wirelessly coupled to the fluidic supply and analysis unit 110 via Bluetooth®, Wi-Fi®, infrared, cellular communication, and any other suitable wireless connection. In embodiments, each of the plurality of composite sensing modules 108 are coupled to the fluidic supply and analysis unit 110 through wires via WAN connections, LAN connections, coaxial cables, fiber optics cables, and any other suitable wired connection.

Referring back to FIG. 1, the system 100 may further comprise a demulsifier tank 126 that is configured to introduce demulsifier fluid to the horizontally oriented fluidic piping of the upper fluidic junction 122 before the demulsifier fluid reaches the vertically extending portion of the fluidic separation chamber 102. The system may further comprise a demulsifier valve 128 configured to supply demulsifying agent from the demulsifying tank and is communicatively coupled to the fluidic supply and analysis unit 110. As will be appreciated by those skilled in the art of multiphase fluid processing, a variety of conventional and yet-to-be developed demulsifying agents will be suitable for use within the scope of the present disclosure including, but not limited to, polyol block copolymers, alkoxylated alkyl phenol formaldehyde resins, epoxy resin alkoxylates, silicone polyethers, modified silicone polyethers, and amine-initiated polyol block copolymers.

The system 100 may further comprise a production fluid supply line valve 130 disposed within a production fluid supply line 131 and is fluidly coupled to the fluidic piping 106. The production fluid supply line valve 130 is positioned downstream of the inlet port 118 of the fluidic separation chamber 102. The fluidic supply and analysis unit 110 is in communication with the production fluid supply line valve 130 and is configured to transition the production fluid supply line valve 130 to a closed state so that multiphase production fluid is diverted from the production fluid supply line 131 to the fluidic separation chamber 102 through the fluidic separation chamber valve 104. The fluidic supply and analysis unit 110 is further configured to return the production fluid supply line valve 130 to an open state when a sufficient amount of multiphase production fluid has been diverted to the fluidic separation chamber 102 through the fluidic separation chamber valve 104. In embodiments, the inlet port 118 of the fluidic separation chamber comprises the fluidic separation chamber valve 104.

The fluidic piping 106 may comprise production fluid return piping 132 fluidly coupling the outlet port 120 of the fluidic separation chamber 102 to the production fluid supply line 131 of the fluidic piping 106. The outlet port 120 of the fluidic separation chamber 102 may further comprise a production fluid return valve 134 configured to return multiphase production fluid to the production fluid supply line 131 through the production fluid return piping 132 at a point downstream of the production fluid supply line valve 130.

The production fluid return valve 134 is communicatively coupled to fluidic supply and analysis unit 110.

Figure 3:
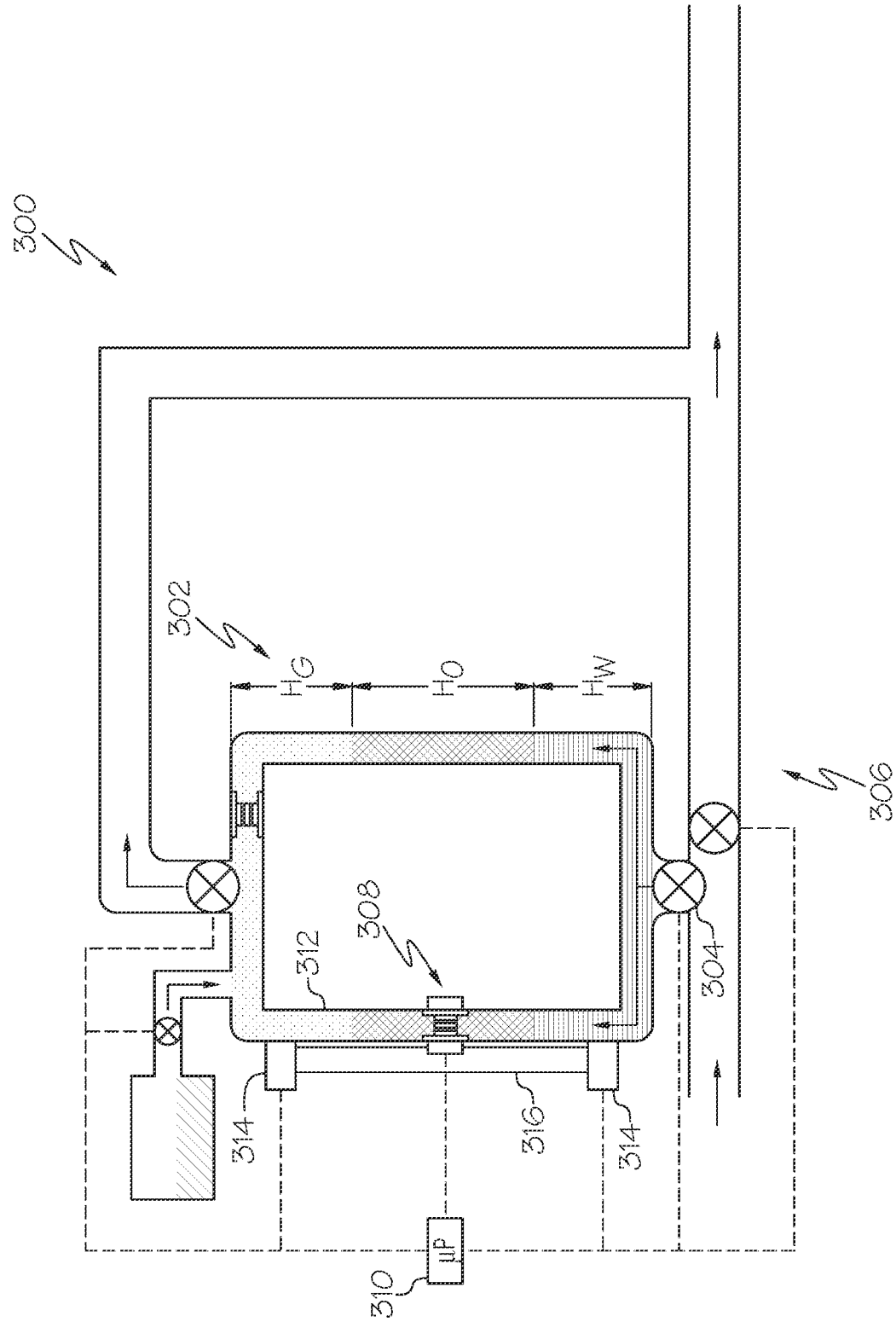
FIG. 3 is a schematic illustration of an alternative system for analyzing a multiphase production fluid according to one or more embodiments of the present disclosure.
Figure 4:
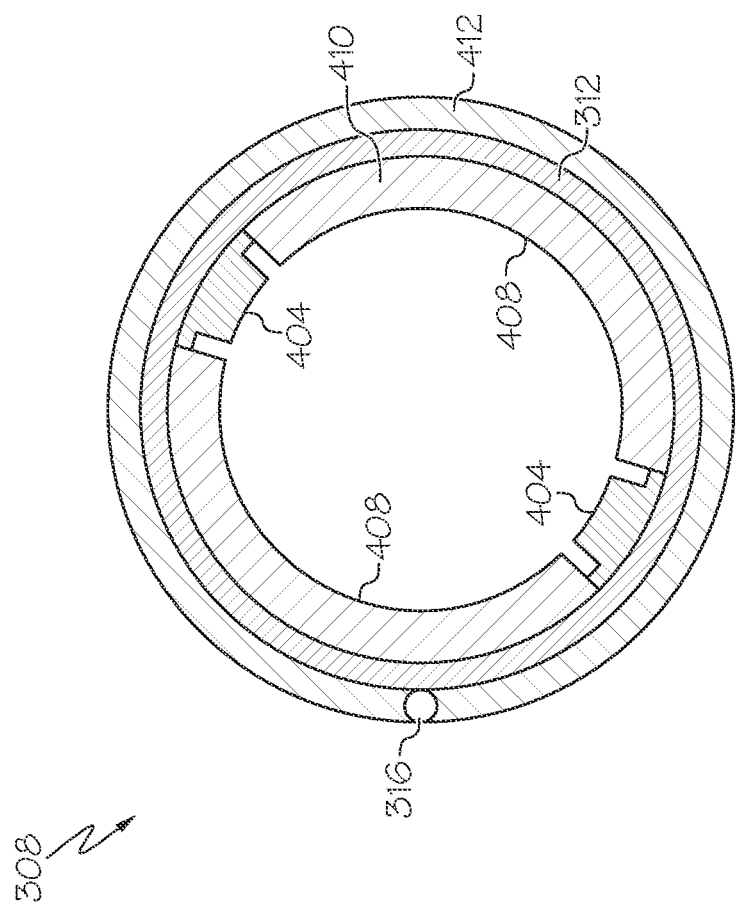
FIG. 4 illustrates aspects of a composite sensing module according to the embodiment of FIG. 3.

Referring now to FIGS. 3-4, a system 300 for analyzing a multiphase production fluid is shown according to various embodiments. The system 300 may share the same components with system 100 as discussed above. The system 300 comprises a fluidic separation chamber 302, a fluidic separation chamber valve 304, fluidic piping 306, a mechanized composite sensing module 308, and a fluidic supply and analysis unit 310. The fluidic piping 306 is configured to supply multiphase production fluid to the fluidic separation chamber 302 through the fluidic separation chamber valve 304

The mechanized composite sensing module 308 comprises opposing inductive sensing elements 404 of an inductive sensor and opposing capacitive sensing elements 408 of a capacitive sensor and is translatable along a vertically extending measurement portion 312 of the fluidic separation chamber 302. The opposing inductive sensing elements 404 are displaced from one another across the vertically extending measurement portion 312 of the fluidic separation chamber 302. Similarly, the opposing capacitive sensing elements 408 are displaced from one another across the vertically extending measurement portion 312 of the fluidic separation chamber 302.

The fluidic supply and analysis unit 310 is in communication with the fluidic separation chamber valve 304 and the mechanized composite sensing module 308. The fluidic supply and analysis unit 310 is configured to communicate with the fluidic separation chamber valve 304 to supply a multiphase production fluid to the fluidic separation chamber 302. The fluidic supply and analysis unit 310 is further configured to communicate with the inductive sensing elements 404 of the mechanized composite sensing module 308 to detect a height $H_W$ of a water phase column in the multiphase production fluid in the fluidic separation chamber 302 during translation of the mechanized composite sensing module 308 along the vertically extending measurement portion 312 of the fluidic separation chamber 302. The fluidic supply and analysis unit 310 is further configured to communicate with the capacitive sensing elements 408 of the mechanized composite sensing module 308 to detect a height $H_O$ of an oil phase column in the multiphase production fluid in the fluidic separation chamber 302 during translation of the mechanized composite sensing module 308 along the vertically extending measurement portion 312 of the fluidic separation chamber 302. The fluidic supply and analysis unit 310 is further configured to communicate with the capacitive sensing elements 408 of the mechanized composite sensing module 308 to detect a height $H_G$ of a gas phase column in the multiphase production fluid in the fluidic separation chamber 302 during translation of the mechanized composite sensing module 308 along the vertically extending measurement portion 312 of the fluidic separation chamber 302. The fluidic supply and analysis unit 310 is further configured to convert the height $H_W$ of the water phase column, the height $H_O$ of the oil phase column, and the height $H_G$ of the gas phase column to production fluid phase volume fraction data, production fluid phase flow rate data, or both.

The mechanized composite sensing module 308 further comprises a measuring module 410 disposed on an interior circumference of the vertically extending measurement portion 312 of the fluidic separation chamber 302. The measuring module 410 comprises the opposing inductive sensing elements 404 of the inductive sensor and the opposing capacitive sensing elements 408 of the capacitive sensor.

The mechanized composite sensing module 308 further comprises a communicating module 412 disposed on an exterior circumference of the vertically extending measurement portion 312 of the fluidic separation chamber 302.

The fluidic supply and analysis unit 310 is in communication with the mechanized composite sensing module 308 via the communicating module 412. The communicating module 412 may be wirelessly coupled to the fluidic supply and analysis unit 310 via Bluetooth®, Wi-Fi®, infrared, cellular communication, and any other suitable wireless connection.

The communicating module 412 and the measuring module 410 are movably coupled such that translation of the communicating module 412 along the exterior circumference of the vertically extending measurement portion 312 of the fluidic separation chamber 302 results in the movement of the measuring module 410 along the interior circumference of the vertically extending measurement portion 312 of the fluidic separation chamber 302.

The system 300 may further comprise a motorized element 314 and a cable 316. The cable 316 extends parallel to the vertically extending measurement portion 312 of the fluidic separation chamber 302. A portion of the cable 316 may extend through a through-hole aperture disposed in the communicating module 412. In this way, the cable 316 mechanically links the motorized element 314 to the communicating module 412 to facilitate movement of the communicating module 412 along the vertically extending measurement portion 312 of the fluidic separation chamber 302.

The fluidic supply and analysis unit 310 is further configured to communicate with the motorized element 314 to translate the mechanized composite sensing module 308 along the vertically extending measurement portion 312 of the fluidic separation chamber 302 by operatively translating the cable 316.

The measuring module 410 may comprise a magnetic exterior surface and the communicating module 412 may comprise a magnetic interior surface, thereby movably coupling the measuring module 410 to the communicating module 412.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for analyzing a multiphase production fluid, the system comprising:
   a fluidic separation chamber;
   a fluidic separation chamber valve;
   fluidic piping configured to supply multiphase production fluid to the fluidic separation chamber through the fluidic separation chamber valve;
   a plurality of composite sensing modules vertically spaced within the fluidic separation chamber, each of the composite sensing modules comprising an inductive sensor comprising opposing inductive sensing elements displaced from one another across a vertically extending measurement portion of the fluidic separation chamber, and a capacitive sensor comprising opposing capacitive sensing elements displaced from one another across the vertically extending measurement portion of the fluidic separation chamber; and
   a fluidic supply and analysis unit in communication with the fluidic separation chamber valve and the plurality of composite sensing modules, the fluidic supply and analysis unit configured to
   communicate with the fluidic separation chamber valve to supply a multiphase production fluid to the fluidic separation chamber,
   communicate with the inductive sensor of each of the plurality of composite sensing modules to detect a height $H_W$ of a water phase column in the multiphase production fluid in the fluidic separation chamber,
   communicate with the capacitive sensor of each of the plurality of composite sensing modules to detect a height $H_O$ of an oil phase column in the multiphase production fluid in the fluidic separation chamber,
   communicate with the capacitive sensor of each of the plurality of composite sensing modules to detect a height $H_G$ of a gas phase column in the multiphase production fluid in the fluidic separation chamber, and
   convert the height $H_W$ of the water phase column, the height $H_O$ of the oil phase column, and the height $H_G$ of the gas phase column to production fluid phase volume fraction data, production fluid phase flow rate data, or both.

2. The system of claim 1, wherein each of the plurality of composite sensing modules are wirelessly coupled to the fluidic supply and analysis unit.

3. The system of claim 1, wherein the fluidic separation chamber comprises:
   a vertically extending dampening portion;
   a lower fluidic junction positioned vertically below, and fluidly coupling, the vertically extending measurement portion and the vertically extending dampening portion; and
   an inlet port fluidly coupled to the vertically extending dampening portion and the vertically extending measurement portion through the lower fluidic junction.

4. The system of claim 3, wherein the vertically extending measurement portion, the vertically extending dampening portion, and the lower fluidic junction are configured such that:
   multiphase production fluid supplied to the fluidic separation chamber through the inlet port is free to flow into the vertically extending measurement portion and the vertically extending dampening portion through the lower fluidic junction; and the supplied multiphase production fluid assumes a dampened oscillating flow across the lower fluidic junction to force columnar dampening in the vertically extending measurement portion.

5. The system of claim 3, wherein the lower fluidic junction comprises a linear length of horizontally oriented fluidic piping.

6. The system of claim 3, wherein:

the fluidic separation chamber comprises an outlet port fluidly coupled to the vertically extending dampening portion and the vertically extending measurement portion; and the outlet port is vertically displaced from the inlet port such that the inlet port and the outlet port are positioned vertically beyond opposite ends of the vertically extending measurement portion and the vertically extending dampening portion.

7. The system of claim 3, wherein:

the fluidic separation chamber comprises an upper fluidic junction positioned vertically above, and fluidly coupling, the vertically extending measurement portion and the vertically extending dampening portion;

an outlet port fluidly coupled to the vertically extending dampening portion and the vertically extending measurement portion through the upper fluidic junction.

8. The system of claim 7, wherein the upper fluidic junction comprises a linear length of horizontally oriented fluidic piping.

9. The system of claim 8, wherein an additional composite sensing module is disposed along the linear length of horizontally oriented fluidic piping of the upper fluidic junction.

10. The system of claim 9, wherein the system further comprises a demulsifier tank that is configured to introduce demulsifier fluid to the horizontally oriented fluidic piping of the upper fluidic junction before the demulsifier fluid reaches the vertically extending measurement portion of the fluidic separation chamber.

11. The system of claim 3, wherein the vertically extending dampening portion is parallel to the vertically extending measurement portion of the fluidic separation chamber.

12. The system of claim 3, wherein the plurality of composite sensing modules are disposed both along the vertically extending measurement portion and along the vertically extending dampening portion.

13. The system of claim 3, wherein the vertically extending measurement portion and the vertically extending dampening portion of the fluidic separation chamber comprise cylindrical cross sections.

14. The system of claim 1, wherein the fluidic separation chamber comprises:

a vertically extending dampening portion parallel to the vertically extending measurement portion of the fluidic separation chamber;

a lower fluidic junction comprising a linear length of horizontally oriented fluidic piping, the lower fluidic junction positioned vertically below, and fluidly coupling, the vertically extending measurement portion and the vertically extending dampening portion; and an inlet port fluidly coupled to the vertically extending dampening portion and the vertically extending measurement portion through the lower fluidic junction, wherein the vertically extending measurement portion, the vertically extending dampening portion, and the lower fluidic junction are configured such that:

multiphase production fluid supplied to the fluidic separation chamber through the inlet port is free to flow into the vertically extending measurement portion and the vertically extending dampening portion through the lower fluidic junction; and the supplied multiphase production fluid assumes a dampened oscillating flow across the lower fluidic junction to force columnar dampening in the vertically extending measurement portion.

15. The system of claim 1, further comprising a production fluid supply line valve disposed within a production fluid supply line fluidly coupled to the fluidic piping, the production fluid supply line valve positioned downstream of an inlet port of the fluidic separation chamber.

16. The system of claim 15, wherein the fluidic supply and analysis unit is in communication with the production fluid supply line valve and is configured to:

transition the production fluid supply line valve to a closed state so that multiphase production fluid is diverted from the production fluid supply line to the fluidic separation chamber through the fluidic separation chamber valve; and return the production fluid supply line valve to an open state when a sufficient amount of multiphase production fluid has been diverted to the fluidic separation chamber through the fluidic separation chamber valve.

17. The system of claim 15, wherein the inlet port of the fluidic separation chamber comprises the fluidic separation chamber valve.

18. The system of claim 15, wherein:

the fluidic piping further comprises production fluid return piping fluidly coupling an outlet port of the fluidic separation chamber to the production fluid supply line of the fluidic piping; and the outlet port of the fluidic separation chamber comprises a production fluid return valve configured to return multiphase production fluid to the production fluid supply line through the production fluid return piping at a point downstream of the production fluid supply line valve.

19. The system of claim 1, wherein the fluidic supply and analysis unit is configured to convert the height $H_W$ of the water phase column, the height $H_O$ of the oil phase column, the height $H_G$ of the gas phase column to production fluid phase volume fraction data.

20. The system of claim 19, wherein the fluidic supply and analysis unit is further configured to calculate production fluid phase flow rate data using the phase volume fraction data and a cross-sectional area A of the fluidic piping, the calculation comprising the product:

$$A \times (H_W + H_O + H_G).$$

* * * * *